(12) United States Patent
Burns et al.

(10) Patent No.: US 11,471,094 B2
(45) Date of Patent: Oct. 18, 2022

(54) DETECTION OF TISSUE DAMAGE

(71) Applicant: Bruin Biometrics, LLC, Los Angeles, CA (US)

(72) Inventors: Martin F. Burns, Los Angeles, CA (US); Graham O. Ross, Oceanside, CA (US)

(73) Assignee: BRUIN BIOMETRICS, LLC, Los Angeles, CA (US)

( * ) Notice: Subject to any disclaimer, the term of this patent is extended or adjusted under 35 U.S.C. 154(b) by 924 days.

(21) Appl. No.: 16/271,040

(22) Filed: Feb. 8, 2019

(65) Prior Publication Data

US 2019/0246972 A1    Aug. 15, 2019

Related U.S. Application Data

(60) Provisional application No. 62/628,676, filed on Feb. 9, 2018.

(51) Int. Cl.

| | |
|---|---|
| A61B 5/053 | (2021.01) |
| A61F 5/44 | (2006.01) |
| A61B 5/00 | (2006.01) |
| A61J 15/00 | (2006.01) |
| A61M 5/172 | (2006.01) |
| A61M 16/04 | (2006.01) |
| A61M 16/06 | (2006.01) |
| A61M 25/00 | (2006.01) |
| A61B 5/0531 | (2021.01) |
| A61B 5/0537 | (2021.01) |
| A61F 5/055 | (2006.01) |

(52) U.S. Cl.
CPC ............ *A61B 5/447* (2013.01); *A61B 5/0531* (2013.01); *A61B 5/0537* (2013.01); *A61B 5/443* (2013.01); *A61B 5/4836* (2013.01); *A61B 5/6843* (2013.01); *A61B 5/7282* (2013.01); *A61F 5/055* (2013.01); *A61F 5/44* (2013.01); *A61J 15/0003* (2013.01); *A61J 15/0084* (2015.05); *A61M 5/1723* (2013.01); *A61M 16/0465* (2013.01); *A61M 16/0497* (2013.01); *A61M 16/0666* (2013.01); *A61M 25/0017* (2013.01); *A61B 2562/0214* (2013.01); *A61B 2562/043* (2013.01)

(58) Field of Classification Search
CPC ..... A61B 5/0531; A61B 5/0537; A61B 5/443; A61B 5/445; A61B 5/447; A61B 5/7282; A61J 15/0003; A61J 15/0084; A61M 16/0666; A61M 16/0683
See application file for complete search history.

(56) References Cited

U.S. PATENT DOCUMENTS

| | | | |
|---|---|---|---|
| 3,851,641 | A | 12/1974 | Toole et al. |
| 4,295,009 | A | 10/1981 | Weidler |

(Continued)

FOREIGN PATENT DOCUMENTS

| | | |
|---|---|---|
| CA | 2811609 | 11/2011 |
| CA | 2609842 C | 10/2016 |

(Continued)

OTHER PUBLICATIONS

Alanen, "Measurement of Hydration in the Stratum Corneum with the MoistureMeter and Comparison with the Corneometer," *Skin Research and Technology*, 10:32-31 (2004).

(Continued)

*Primary Examiner* — Jon Eric C Morales
(74) *Attorney, Agent, or Firm* — Arnold & Porter Kaye Scholer LLP

(57) ABSTRACT

Methods and apparatus for detection of tissue damage in patients using a medical device for an extended period of time are disclosed.

31 Claims, 9 Drawing Sheets

(56) References Cited

U.S. PATENT DOCUMENTS

| | | |
|---|---|---|
| 4,557,271 A | 12/1985 | Stoller et al. |
| 4,857,716 A | 8/1989 | Gombrich et al. |
| 4,860,753 A | 8/1989 | Amerena |
| 5,073,126 A | 12/1991 | Kikuchi et al. |
| 5,284,150 A | 2/1994 | Butterfield et al. |
| 5,292,341 A | 3/1994 | Snell |
| 5,367,789 A | 11/1994 | Lamont |
| 5,815,416 A | 9/1998 | Liebmann et al. |
| 5,904,581 A | 5/1999 | Pope et al. |
| 6,223,088 B1 | 4/2001 | Scharnberg et al. |
| 6,312,263 B1 | 11/2001 | Higuchi et al. |
| 6,330,479 B1 | 12/2001 | Stauffer |
| 6,370,426 B1 | 4/2002 | Campbell et al. |
| 6,434,422 B1 | 8/2002 | Tomoda et al. |
| 6,577,700 B1 | 6/2003 | Fan et al. |
| 6,634,045 B1 | 10/2003 | DuDonis et al. |
| 6,738,798 B1 | 5/2004 | Ploetz et al. |
| 6,756,793 B2 | 6/2004 | Hirono et al. |
| 6,963,772 B2 | 11/2005 | Bloom et al. |
| 7,079,899 B2 | 7/2006 | Petrofsky |
| 7,315,767 B2 | 1/2008 | Caduff et al. |
| 7,402,135 B2 | 7/2008 | Leveque et al. |
| 7,783,344 B2 | 8/2010 | Lackey et al. |
| 8,011,041 B2 | 9/2011 | Hann |
| 8,060,315 B2 | 11/2011 | Brosette et al. |
| 8,355,925 B2 | 1/2013 | Rothman et al. |
| 8,390,583 B2 | 3/2013 | Forutanpour et al. |
| 8,494,617 B2 | 7/2013 | Baker, Jr. et al. |
| 8,925,392 B2 | 1/2015 | Esposito et al. |
| 9,028,407 B1 | 5/2015 | Bennett-Guerrero |
| 9,095,305 B2 | 8/2015 | Engler et al. |
| 9,220,455 B2 | 12/2015 | Sarrafzadeh et al. |
| 9,271,676 B2 | 3/2016 | Alanen et al. |
| 9,398,879 B2 | 7/2016 | Sarrafzadeh et al. |
| 9,675,289 B2 | 6/2017 | Heaton |
| 9,763,596 B2 | 9/2017 | Tonar et al. |
| 9,949,683 B2 | 4/2018 | Afentakis |
| 9,980,673 B2 | 5/2018 | Sarrafzadeh et al. |
| 10,085,643 B2 | 10/2018 | Bandic et al. |
| 10,166,387 B2 | 1/2019 | Bergelin et al. |
| 10,178,961 B2 | 1/2019 | Tonar et al. |
| 10,182,740 B2 | 1/2019 | Tonar et al. |
| 10,188,340 B2 | 1/2019 | Sarrafzadeh et al. |
| 10,194,856 B2 | 2/2019 | Afentakis et al. |
| 10,206,604 B2 | 2/2019 | Bergelin et al. |
| 10,226,187 B2 | 3/2019 | Al-Ali et al. |
| 10,278,636 B2 | 5/2019 | Wu et al. |
| 10,285,898 B2 | 5/2019 | Douglas et al. |
| 10,307,060 B2 | 6/2019 | Tran |
| 10,342,482 B1 | 7/2019 | Lisy et al. |
| 10,383,527 B2 | 8/2019 | Al-Ali |
| 10,420,602 B2 | 9/2019 | Horton et al. |
| 10,441,185 B2 | 10/2019 | Rogers et al. |
| 10,448,844 B2 | 10/2019 | Al-Ali et al. |
| 10,463,293 B2 | 11/2019 | Maharbiz et al. |
| 10,485,447 B2 | 11/2019 | Tonar et al. |
| 10,950,960 B2 | 3/2021 | Burns et al. |
| 11,191,477 B2 | 12/2021 | Burns |
| 11,253,192 B2 | 2/2022 | Sarrafzadeh et al. |
| 11,284,810 B2 | 3/2022 | Tonar et al. |
| 11,304,652 B2 | 4/2022 | Burns et al. |
| 2001/0051783 A1 | 12/2001 | Edwards et al. |
| 2002/0016535 A1 | 2/2002 | Martin et al. |
| 2002/0070866 A1 | 6/2002 | Newham |
| 2002/0112898 A1 | 8/2002 | Honda et al. |
| 2002/0143262 A1 | 10/2002 | Bardy |
| 2003/0009244 A1 | 1/2003 | Engleson et al. |
| 2003/0036674 A1 | 2/2003 | Bouton |
| 2003/0036713 A1 | 2/2003 | Bouton et al. |
| 2003/0110662 A1 | 6/2003 | Gilman et al. |
| 2003/0116447 A1 | 6/2003 | Surridge et al. |
| 2003/0139255 A1 | 7/2003 | Lina |
| 2004/0041029 A1 | 3/2004 | Postman et al. |
| 2004/0046668 A1 | 3/2004 | Smith et al. |
| 2004/0054298 A1 | 3/2004 | Masuo et al. |
| 2004/0080325 A1 | 4/2004 | Ogura |
| 2004/0133092 A1 | 7/2004 | Kain |
| 2004/0171962 A1 | 9/2004 | Leveque et al. |
| 2004/0176754 A1 | 9/2004 | Island et al. |
| 2004/0236200 A1 | 11/2004 | Say et al. |
| 2004/0254457 A1 | 12/2004 | Van Der Weide |
| 2005/0027175 A1 | 2/2005 | Yang |
| 2005/0070778 A1 | 3/2005 | Lackey et al. |
| 2005/0086072 A1 | 4/2005 | Fox, Jr. et al. |
| 2005/0096513 A1 | 5/2005 | Ozguz et al. |
| 2005/0177061 A1 | 8/2005 | Alanen et al. |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox, Jr. et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0206013 A1 | 9/2006 | Rothman et al. |
| 2007/0106172 A1 | 5/2007 | Abreu |
| 2007/0179585 A1 | 8/2007 | Chandler et al. |
| 2007/0191273 A1 | 8/2007 | Ambati et al. |
| 2007/0213700 A1 | 9/2007 | Davison et al. |
| 2008/0009764 A1 | 1/2008 | Davies |
| 2008/0015894 A1 | 1/2008 | Miller et al. |
| 2008/0048680 A1 | 2/2008 | Hargreaves et al. |
| 2008/0259577 A1 | 10/2008 | Hu et al. |
| 2008/0278336 A1 | 11/2008 | Ortega et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0285785 A1 | 11/2009 | Jimi et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0268111 A1 | 10/2010 | Drinan et al. |
| 2010/0298687 A1 | 11/2010 | Yoo et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0046505 A1 | 2/2011 | Cornish et al. |
| 2011/0160548 A1 | 6/2011 | Forster |
| 2011/0184264 A1 | 7/2011 | Galasso, Jr. et al. |
| 2011/0191122 A1 | 8/2011 | Kharraz Tavakol et al. |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0288397 A1 | 6/2014 | Sarrafzadeh et al. |
| 2014/0200486 A1 | 7/2014 | Bechtel et al. |
| 2014/0273025 A1 | 9/2014 | Hurskainen et al. |
| 2014/0275823 A1 | 9/2014 | Lane et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |

| | | | | | | |
|---|---|---|---|---|---|---|
| 2015/0009168 A1 | 1/2015 | Levesque et al. | GB | 2584808 A | 12/2020 | |
| 2015/0094548 A1 | 4/2015 | Sabatini et al. | JP | 2003-169788 A | 6/2003 | |
| 2015/0186607 A1 | 7/2015 | Gileijnse et al. | JP | 2003-290166 A | 10/2003 | |
| 2015/0230863 A1 | 8/2015 | Youngquist et al. | JP | 2005-52227 | 3/2005 | |
| 2015/0343173 A1 | 12/2015 | Tobescu et al. | JP | 4418419 | 2/2010 | |
| 2015/0363567 A1 | 12/2015 | Pettus | JP | 2013-198639 A | 10/2013 | |
| 2015/0366499 A1 | 12/2015 | Sarrafzadeh et al. | KR | 10-2014-0058445 | 5/2014 | |
| 2015/0371522 A1 | 12/2015 | Mravyan et al. | WO | 96/10951 A1 | 4/1996 | |
| 2016/0015962 A1 | 1/2016 | Shokoueinejad Maragheh et al. | WO | 2001/054580 A1 | 8/2001 | |
| 2016/0038055 A1 | 2/2016 | Wheeler et al. | WO | 2002/080770 A1 | 10/2002 | |
| 2016/0058342 A1 | 3/2016 | Maiz-Aguinaga et al. | WO | 2004/105602 A1 | 12/2004 | |
| 2016/0072308 A1 | 3/2016 | Nyberg et al. | WO | 2006/029035 A1 | 3/2006 | |
| 2016/0100790 A1 | 4/2016 | Cantu et al. | WO | 2007/098762 A1 | 9/2007 | |
| 2016/0101282 A1 | 4/2016 | Bergelin et al. | WO | 2009/144615 A1 | 12/2009 | |
| 2016/0174871 A1 | 6/2016 | Sarrafzadeh et al. | WO | 2010/060102 A2 | 5/2010 | |
| 2016/0220172 A1 | 8/2016 | Sarrafzadeh et al. | WO | 2011/022418 A2 | 2/2011 | |
| 2016/0270672 A1 | 9/2016 | Chen et al. | WO | 2011/080080 A1 | 7/2011 | |
| 2016/0270968 A1 | 9/2016 | Stanford et al. | WO | 2011/080262 A1 | 7/2011 | |
| 2016/0278692 A1 | 9/2016 | Larson et al. | WO | 2011/091517 A1 | 8/2011 | |
| 2016/0296268 A1 | 10/2016 | Gee et al. | WO | 2011/143071 A2 | 11/2011 | |
| 2016/0310034 A1 | 10/2016 | Tonar et al. | WO | 2013/116242 A2 | 8/2013 | |
| 2016/0338591 A1 | 11/2016 | Lachenbruch et al. | WO | 2014/186894 A1 | 11/2014 | |
| 2017/0007153 A1 | 1/2017 | Tonar et al. | WO | 2015/003015 A2 | 1/2015 | |
| 2017/0014044 A1 | 1/2017 | Tonar et al. | WO | 2015/077838 A1 | 6/2015 | |
| 2017/0014045 A1 | 1/2017 | Tonar et al. | WO | 2015/168720 A1 | 11/2015 | |
| 2017/0156658 A1 | 6/2017 | Maharbiz et al. | WO | 2015/169911 A1 | 11/2015 | |
| 2017/0172489 A1 | 6/2017 | Afentakis | WO | 2015/195720 A1 | 12/2015 | |
| 2017/0188841 A1 | 7/2017 | Ma et al. | WO | 2016/172263 A1 | 10/2016 | |
| 2017/0238849 A1 | 8/2017 | Chapman et al. | WO | 2016/172264 A1 | 10/2016 | |
| 2017/0255812 A1 | 9/2017 | Kwon | WO | 2017/032393 | 3/2017 | |
| 2017/0311807 A1 | 11/2017 | Fu et al. | WO | 2017/214188 A1 | 12/2017 | |
| 2017/0319073 A1 | 11/2017 | DiMaio et al. | WO | 2017/218818 A2 | 12/2017 | |
| 2018/0020058 A1 | 1/2018 | Martines et al. | WO | 2018/071715 A1 | 4/2018 | |
| 2018/0045725 A1 | 2/2018 | Yoo et al. | WO | 2018/077560 A1 | 5/2018 | |
| 2018/0220924 A1 | 8/2018 | Burns et al. | WO | 2018/115461 A1 | 6/2018 | |
| 2018/0220953 A1 | 8/2018 | Burns et al. | WO | 2018/144938 | 8/2018 | |
| 2018/0220954 A1 | 8/2018 | Burns et al. | WO | 2018/144941 | 8/2018 | |
| 2018/0220961 A1 | 8/2018 | Burns et al. | WO | 2018/144943 | 8/2018 | |
| 2018/0360344 A1 | 12/2018 | Burns et al. | WO | 2018/144946 | 8/2018 | |
| 2019/0000352 A1 | 1/2019 | Everett et al. | WO | 2018/189265 A1 | 10/2018 | |
| 2019/0038133 A1 | 2/2019 | Tran | WO | 2018/209100 A1 | 11/2018 | |
| 2019/0060602 A1 | 2/2019 | Tran et al. | WO | 2018/234443 A1 | 12/2018 | |
| 2019/0104981 A1 | 4/2019 | Sarrafzadeh et al. | WO | 2018/236739 | 12/2018 | |
| 2019/0104982 A1 | 4/2019 | Dunn et al. | WO | 2019/020551 A1 | 1/2019 | |
| 2019/0134396 A1 | 5/2019 | Toth et al. | WO | 2019/030384 A2 | 2/2019 | |
| 2019/0142333 A1 | 5/2019 | Burns et al. | WO | 2019/048624 A1 | 3/2019 | |
| 2019/0147990 A1 | 5/2019 | Burns et al. | WO | 2019/048626 A1 | 3/2019 | |
| 2019/0148901 A1 | 5/2019 | Komoto | WO | 2019/048638 A1 | 3/2019 | |
| 2019/0150882 A1 | 5/2019 | Maharbiz et al. | WO | 2019/072531 A1 | 4/2019 | |
| 2019/0175098 A1 | 6/2019 | Burns et al. | WO | 2019/073389 A1 | 4/2019 | |
| 2019/0192066 A1 | 6/2019 | Schoess et al. | WO | 2019/076967 A2 | 4/2019 | |
| 2019/0282436 A1 | 9/2019 | Douglas et al. | WO | 2019/096828 A1 | 5/2019 | |
| 2019/0290189 A1 | 9/2019 | Sarrafzadeh et al. | WO | 2019/099810 | 5/2019 | |
| 2019/0307360 A1 | 10/2019 | Tonar et al. | WO | 2019/099812 A1 | 5/2019 | |
| 2019/0307405 A1 | 10/2019 | Terry et al. | WO | 2019/113481 | 6/2019 | |
| 2020/0069240 A1 | 3/2020 | Burns | WO | 2019/157290 | 8/2019 | |
| 2020/0069241 A1 | 3/2020 | Burns | WO | 2019/162272 A1 | 8/2019 | |
| 2020/0069242 A1 | 3/2020 | Burns et al. | WO | 2020/014779 A1 | 1/2020 | |
| 2020/0077892 A1 | 3/2020 | Tran | WO | 2020/043806 A1 | 3/2020 | |
| 2020/0078499 A1 | 3/2020 | Gadde et al. | WO | 2020/053290 A1 | 3/2020 | |
| 2020/0093395 A1 | 3/2020 | Tonar et al. | WO | 2020/077100 A1 | 4/2020 | |
| 2020/0100723 A1 | 4/2020 | Burns | WO | 2020/187643 A1 | 9/2020 | |
| 2020/0113488 A1 | 4/2020 | Al-Ali et al. | WO | 2020/187851 A1 | 9/2020 | |
| 2020/0127398 A1 | 4/2020 | Burns et al. | WO | 2020/234429 A2 | 11/2020 | |
| 2020/0296821 A1 | 9/2020 | Trublowski et al. | | | | |
| 2020/0297244 A1 | 9/2020 | Brownhill et al. | | | | |
| 2020/0297255 A1 | 9/2020 | Martinez et al. | | | | |

FOREIGN PATENT DOCUMENTS

| | | |
|---|---|---|
| CN | 204119175 U | 1/2015 |
| CN | 104567657 A | 4/2015 |
| CN | 208111467 U | 11/2018 |
| DE | 102012011212 A1 | 1/2012 |
| EP | 1080687 A1 | 3/2001 |
| EP | 1372475 | 1/2004 |
| EP | 1569553 A1 | 9/2005 |
| EP | 3092946 A1 | 11/2016 |
| EP | 3280488 B1 | 12/2018 |

OTHER PUBLICATIONS

Alberts et al., "The Extracellular Matrix of Animals," *Molecular Biology of the Cell*, 4th ed., pp. 1065-1127 (2002).

Allman et al., "Pressure Ulcer Risk Factors Among Hospitalized Patients with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Deimal Papillae in the Development of Pressure Sores," *World Wide Wounds*, (1999).

Australian Intellectual Property Office, Office Action dated May 1, 2014 for corresponding Australian patent application No. 2011253253 (pp. 1-10) and pending claims (pp. 11-15) pp. 1-15.

Australian Patent Office, Office Action dated Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).

Bates-Jensen et al., "Subepideimal Moisture Predicts Erythema and Stage 1 Pressure Ulcers in Nursing Home Residents: A Pilot Study," *Journal of the American Geriatric Society*, 55:1199-1205 (2007).

Bates-Jensen et al., "Subepideimal moisture differentiates erythema and stage 1 pressure ulcers in nursing home residents," *Wound Repair Regeneration*, 16:189-197 (2008).

Bates-Jensen et al., "Subepidermal Moisture is Associated With Early Pressure Ulcer Damage in Nursing Home Residents With Dark Skin Tones; Pilot Findings," *Journal of Wound Ostomy and Continence Nursing*, 36(3):277-284 (2009).

Bergstrand et al., "Pressure-induced Vasodilation and Reactive Hyperemia at Different Depths in Sacral Tissue Under Clinically Relevant Conditions," *Microcirculation*, 21:761-771 (2014).

Bergstrom et al., "Pressure Ulcers in Adults: Prediction and Prevention," *Clinical Practice Guideline—Quick Reference Guide for Clinicians*, 117 (1992).

Brem et al. "High cost of stage IV pressure ulcers," *American Journal of Surgery*, 200:473-477 (2010).

Brienza et al., "Friction-Induced Skin Injuries—Are They Pressure Ulcers?," *Journal of Wound Ostomy and Continence Nursing*, 42(1):62-64 (2015).

Carmo-Araujo et al., "Ischaemia and reperfusion effects on skeletal muscle tissue: morphological and histochemical studies," *International Journal of Experimental Pathology*, 88:147-154 (2007).

Ceelen et al., "Compression-induced damage and internal tissue strains are related," *Journal of Biomechanics*, 41:3399-3404 (2008).

Ching et al., "Tissue electrical properties monitoring for the prevention of pressure sore," *Prosthetics and Orthotics International*, 35(4):386-394 (2011).

Clendenin et al., "Inter-operator and inter-device agreement and reliability of the SEM Scanner," *Journal of Tissue Viability*, 24(1):17-23 (2015).

De Lorenzo et al., "Predicting body cell mass with bioimpedance by using theoretical methods: a technological review," *Journal of Applied Physiology*, 82(5):1542-1558 (1997).

Demarre et al., "The cost of pressure ulcer prevention and treatment in hospitals and nursing homes in Flanders: A cost-of-illness study," *International Journal of Nursing Studies*, 1-14 (2015).

Dodde et al., "Bioimpedance of soft tissue under compression," *Physiology Measurement*, 33(6):1095-1109 (2012).

DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).

Dupont, "Pyralux® FR Coverlay, Bondply & Sheet Adhesive," webpage, Retrieved from: www2.dupont.com/Pyralux/en_US/produets/adhesives_films/FR/FR_films_html pp. 1-2 (2012).

DuPont, "Pyralux® FR Copper-clad Laminate," webpage, Retrieved from: www2.dupont.com/Pyraluxlen_US/productsllaminate/FR/pyralux_fr.html, pp. 1-2 (2012).

Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).

European Patent Office, ESSR issued on Aug. 22, 2014 for corresponding European Patent Application No. 117811061.4 (pp. 1-7) and pending claims (pp. 3-10) pp. 1-10.

European Patent Office, Office Action dated Jul. 13, 2015, for corresponding European Patent Application No. 117811061.4 (pp. 1-5) and claims (pp. 6-9) pp. 1-9.

Extended European Search Report dated Aug. 19, 2016, in European Patent Application No. 16169670.

Extended European Search Report dated Sep. 19, 2016, in European Patent Application No. 16166483.4.

Extended European Search Report dated Mar. 13, 2017, in European Patent Application No. 16196899.5.

Gabriel, "Compilation of the Dielectric Properties of Body Tissues at Rf and Microwave Frequencies Report," *Occupational and Environmental Health Directorate*, (1996).

Gabriel et al., "The dielectric properties of biological tissues: II. Measurements in the frequency range 10 Hz to 20 GHz," *Physics in Medicine and Biology*, 41:2251-69 (1996).

Gardiner et al., "Incidence of hospital-acquired pressure ulcers—a population-based cohort study," *International Wound Journal*, 11(6):696-700 (2014).

Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).

Gonzalez-Correa et al., "Electrical bioimpedanee readings increase with higher pressure applied to the measuring probe," *Physiology Measurement*, 26:S39-S47 (2005).

Guihan et al., "Assessing the feasibility of subepideimal moisture to predict erythema and stage 1 pressure ulcers in persons with spinal cord injury: A pilot study," *Journal of Spinal Cord Medicine*, 35(1):46-52 (2012).

Harrow, "Subepidermal moisture surrounding pressure ulcers in persons with a spinal cord injury: A pilot study," *Journal of Spinal Cord Medicine*, 37(6):719-728 (2014).

Houwing et al., "Pressure-induced skin lesions in pigs: reperfusion injury and the effects of vitamin E," *Journal of Wound Care*, 9(1):36-40 (2000).

Huang et al., "A device for skin moisture and environment humidity detection," *Sensors and Actuators B: Chemical*, 206-212 (2008).

International Search Report dated Apr. 12, 2018, issued in International Patent Application No. PCT/US2018/016731.

International Search Report dated Apr. 12, 2018, issued in International Patent Application No. PCT/US2018/016738.

International Search Report dated Apr. 26, 2018, issued in International Patent Application No. PCT/US2018/016741.

International Search Report dated Jul. 12, 2018, issued in International Patent Application No. PCT/US2018/016736.

International Search Report dated Sep. 10, 2018, issued in International Patent Application No. PCT/US2018/038055.

International Search Report dated Jan. 29, 2019, issued in International Patent Application No. PCT/US2018/061494.

International Search Report dated Feb. 5, 2019, issued in International Patent Application No. PCT/US2018/064527.

International Search Report dated Feb. 11, 2019, issued in International Patent Application No. PCT/US2018/061497.

International Search Report dated May 29, 2019, issued in International Patent Application No. PCT/US2019/017226.

International Search Report and Written Opinion dated Feb. 9, 2012 for International Patent Application No. PCT/US2011/035618.

International Search Report and Written Opinion dated Jul. 22, 2016, for International Patent Application No. PCT/US2016/28515.

International Search Report and Written Opinion dated Jul. 26, 2016, for International Patent Application No. PCT/US2016/28516.

Jan et al., "Local cooling reduces skin ischemia under surface pressure in rats: an assessment by wavelet analysis of laser Doppler blood flow oscillations," *Physiology Measurement*, 33(10):1733-1745 (2012).

Jaskowski, "Evaluation of the Healing Process of Skin Wounds by Means of Skin Absolute Value of Electrical Impedance," *Dermatol. Mon.schr.*, 172(4):223-228 (1986).

Jiang et al., "Expression of cytokines, growth factors and apoptosis-related signal molecules in chronic pressure ulcer wounds healing," *Spinal Cord*, 52(2):145-151 (2014).

Jiang et al., "Ischemia-Reperfusion Injury-Induced Histological Changes Affecting Early Stage Pressure Ulcer Development in a Rat model," *Ostomy Wound Management*, 57:55-60 (2011).

Jiricka et al., "Pressure Ulcer Risk factors in an ICU Population," *American Journal of Critical Care*, 4:361-367 (1995).

Kanai et al., "Electrical measurement of fluid distribution in legs and arms," *Medical Progress through Technology Journal*, 12:159-170 (1987).
Kasyua et al., "Potential application of in vivo imaging of impaired lymphatic duct to evaluate the severity of pressure ulcer in mouse model," *Scientific Reports*, 4:4173 (2014).
Lee, "CapSense Best Practices," *Application Note 2394*, 1-10 (2007).
Loerakker et al., "The effects of deformation, ischemia, and reperfusion on the development of muscle damage during prolonged loading," *Journal of Applied Physiology*, 111(4):1168-1177 (2011).
Loerakker et al., "Temporal Effects of Mechanical Loading on Deformation- Induced Damage in Skeletal Muscle Tissue," *Annual Review of Biomedical Engineering*, 38(8):2577-2587 (2010).
Lyder et al., "Quality of Care for Hospitalized Medicare Patients at Risk for Pressure Ulcers," *Archives of Internal Medicine*, 161:1549-1554 (2001).
Martinsen, "Bioimpedance and Bioelectricity Basics," *Elsevier Academic Press*, Chapters 1 and 10 (2015).
Mathiesen et al., "Are labour-intensive efforts to prevent pressure ulcers cost-effective?" *Journal of Medical Economics*, 16(10):1238-1245 (2013).
Matthie et al., "Analytic assessment of the various bioimpedance methods used to estimate body water," *Journal of Applied Physiology*, 84(5):1801-1816 (1998).
Miller et al., "Lymphatic Clearance during Compressive Loading," *Lymphology*, 14(4):161-166 (1981).
Moore et al., "A randomised controlled clinical trial of repositioning, using the 30° tilt, for the prevention of pressure ulcers," *Journal of Clinical Nursing*, 20:2633-2644 (2011).
Moore et al., "Pressure ulcer prevalence and prevention practices in care of the older person in the Republic of Ireland," *Journal of Clinical Nursing*, 21:362-371 (2012).
Moore et al., "A review of PU prevalence and incidence across Scandinavia, Iceland and Ireland (Part I)", *Journal of Wound Care*, 22(7):361-362, 364-368 (2013).
Mulasi, "Bioimpedance at the Bedside: Current Applications, Limitations, and Opportunities," *Nutritional Clinical Practice*, 30(2):180-193 (2015).
National Pressure Ulcer Advisory Panel et al., "Prevention and Treatment of Pressure Ulcers: Clinical Practice Guideline," *Cambridge Media*, (2014).
Nixon et al., "Pathology, diagnosis, and classification of pressure ulcers: comparing clinical and imaging techniques," *Wound Repair and Regeneration*, 13(4):365-372 (2005).
Nuutinen et al., "Validation of a new dielectric device to asses changes of tissue water in skin and subcutaneous fat," *Physiological Measurement*, 25:447-454 (2004).
O'Goshi, "Skin conductance; validation of Skicon-200EX compared to the original model, Skicon-100," *Skin Research and Technology*, 13:13-18 (2007).
Oomens et al., "Pressure Induced Deep Tissue Injury Explained," *Annual Review of Biomedical Engineering*, 43(2):297-305 (2015).
Scallan et al., "Chapter 4: Pathophysiology of Edema Formation," *Capillary Fluid Exchange: Regulation, Functions, and Pathology*, 47-61 (2010).
Schultz et al., "Extracellular matrix: review of its role in acute and chronic wounds," *World Wide Wounds*, 1-20 (2005).
Schwan, "Electrical properties of tissues and cells," *Advances in Biology and Medical Physics*, 15:148-199 (1957).
Sener et al., "Pressure ulcer-induced oxidative organ injury is ameliorated by beta-glucan treatment in rats," *International Immunopharmacology*, 6(5):724-732 (2006).
Sewchuck et al., "Prevention and Early Detection of Pressure Ulcers in Patients Undergoing Cardiac Surgery," *AORN Journal*, 84(1):75-96 (2006).
Sprigle et al., "Analysis of Localized Erythema Using Clinical Indicators and Spectroscopy," *Ostomy Wound Management*, 49:42-52 (2003).
Stekelenburg et al., "Deep Tissue Injury: How Deep is Our Understanding?" *Archives of Physical Medicine Rehabilitation*, 89(7):1410-1413 (2008).
Stekelenburg et al., "Role of ischemia and deformation in the onset of compression-induced deep tissue injury: MRI-based studies in a rat model," *Journal of Applied Physiology*, 102:2002-2011 (2007).
Swisher et al., "Impedance sensing device enables early detection of pressure ulcers in vivo," *Nature Communications*, 6:6575-6584 (2015).
Thomas et al., "Hospital-Acquired Pressure Ulcers and Risk of Death," *Journal of the American Geriatrics Society*, 44:1435-1440 (1996).
Valentinuzzi et al., "Bioelectrical Impedance Techniques in Medicine. Part II: Monitoring of Physiological Events by Impedance," *Critical Reviews in Biomedical Engineering*, 24(4-6):353-466 (1996).
Vangilder et al., "Results of Nine International Pressure Ulcer Prevalence Surveys: 1989 to 2005," *Ostomy Wound Management*, 54(2):40-54 (2008).
Wagner et al., "Bioelectrical Impedance as a Discriminator of Pressure Ulcer Risk," *Advances in Wound Care*, 9(2):30-37 (1996).
Wang, "Biomedical System for Monitoring Pressure Ulcer Development," UCLA Electronic Theses and Dissertations, California, USA, pp. 1-123 (2013).
Watanabe et al., "CT analysis of the use of the electrical impedance technique to estimate local oedema in the extremities in patients with lymphatic obstruction," *Medical and Biological Engineering and Computing*, 36(1):60-65 (1998).
Weiss, "Tissue destruction by neutrophils," *The New England Journal of Medicine*, 320(6):365-76 (1989).
Bates-Jensen et al., "Subepidermal Moisture Detection of Pressure Induced Tissue Damage on the Trunk: The Pressure Ulcer Detection Study Outcomes," *Wound Repair and Regeneration*, 25:502-511 (2017).
Berggren, "Capacitive Biosensors," *Electroanalysis*, 13(3):173-180 (2001).
Black et al., "Differential Diagnosis of Suspected Deep Tissue Injury," *International Wound Journal*, 13(4):531-539 (2015).
Brem et al., "Protocol for the Successful Treatment of Pressure Ulcers," *The American Journal of Surgery*, 188 (Suppl. to Jul. 2004):9S-17S (2004).
Extended European Search Report dated Oct. 25, 2019, in European Patent Application No. 19186393.5.
Extended European Search Report dated Nov. 19, 2019, in European Patent Application No. 19190000.0.
Extended European Search Report dated Feb. 6, 2020, in European Patent Application No. 18748733.5.
Extended European Search Report dated Feb. 10, 2020, in European Patent Application No. 18748025.6.
Extended European Search Report dated Feb. 10, 2020, in European Patent Application No. 18748512.3.
Extended European Search Report dated Jun. 24, 2020, in European Patent Application No. 18747707.0.
Extended European Search Report dated Mar. 17, 2022, in European Patent Application No. 19838240.0.
Extended European Search Report dated May 24, 2022, in European Patent Application No. 19871332.3.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).
Great Britain Search Report dated Apr. 27, 2020, in Great Britain Patent Application No. GB2002889.0.
Great Britain Search Report dated Jun. 28, 2021, in Great Britain Patent Application No. GB2106848.1.
Great Britain Search Report dated Feb. 9, 2022, in Great Britain Patent Application No. GB2118088.0.
Great Britain Search Report dated Feb. 14, 2022, in Great Britain Patent Application No. GB2118092.2.
Hou, "Section IV. Osteofascial Compartment Syndrome," *Limbs Trauma*, 7:215-217 (2016).
International Search Report dated Mar. 9, 2020, issued in International Patent Application No. PCT/US2019/055655.
International Search Report dated Dec. 8, 2020, issued in International Patent Application PCT/US2020/051134.

International Search Report dated Aug. 17, 2021, issued in International Patent Application PCT/US2021/023818.

International Search Report dated May 13, 2022, issued in International Patent Application PCT/US2022/014913.

Liu et al., "A Systematic Review of Electrical Stimulation for Pressure Ulcer Prevention and Treatment in People with Spinal Cord Injuries," *The Journal of Spinal Cord Medicine*, 37(6):703-718 (2014).

Moore et al., "Subepiderrnal Moisture (SEM) and Bioimpedance: A Literature Review of a Novel Method for Early Detection of Pressure-Induced Tissue Damage (Pressure Ulcers)," *International Wound Journal*, 14(2):331-337 (2016).

Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017).

Moore et al., "SEM Scanner Made Easy," *Wounds International*, pp. 1-6, available at www.woundsinternational.com (2018).

Oliveira, "The Accuracy of Ultrasound, Thermography, Photography and Sub-Epidermal Moisture as a Predictor of Pressure Ulcer Presence—a Systematic Review," RCSI, School of Nursing thesis (2015).

Rotaru et al., "Friction between Human Skin and Medical Textiles for Decubitus Prevention," *Tribology International*, 65:91-96 (2013).

Saxena, *The Pocket Doctor: Obstetrics & Gynecology*, pp. 76-77 (2017).

Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49pp. (Aug. 2019).

Supplementary Partial European Search Report dated Jan. 27, 2020, in European Patent Application No. 18747707.

Supplementary European Search Report dated Jul. 13, 2021, in European Patent Application No. 18887039.

Supplementary European Search Report dated Oct. 1, 2021, in European Patent Application No. 19751130.

Thomas, "Prevention and Treatment of Pressure Ulcers," *J. Am. Med. Dir. Assoc.*, 7:46-59 (2006).

Tmong et al., "Pressure Ulcer Prevention in the Hospital Setting Using Silicone Foam Dressings," *Cureus*, 8(8):e730, pp. 1-6 (2016).

Tur et al., "Topical Hydrogen Peroxide Treatment of Ischemic Ulcers in the Guinea Pig: Blood Recmitment in Multiple Skin Sites," *J. Am. Acad. Dermatol.*, 33:217-221 (1995).

Vowden et al., "Diabetic Foot Ulcer or Pressure Ulcer? That is the Question," *The Diabetic Foot Journal*, 18:62-66 (2015).

Wang et al., "A Wireless Biomedical Instalment for Evidence-Based Tissue Wound Characterization," *Wireless Health*, pp. 222-223 (2010).

Yang, *Handbook of Practical Burn Surgery*, p. 48 (2008).

Zanibbi, "Pattern Recognition: An Overview," downloaded from https://www.cs.rit.edu/~rlaz/prec20092/slides/Overview.pdf, 30 pp. (2010).

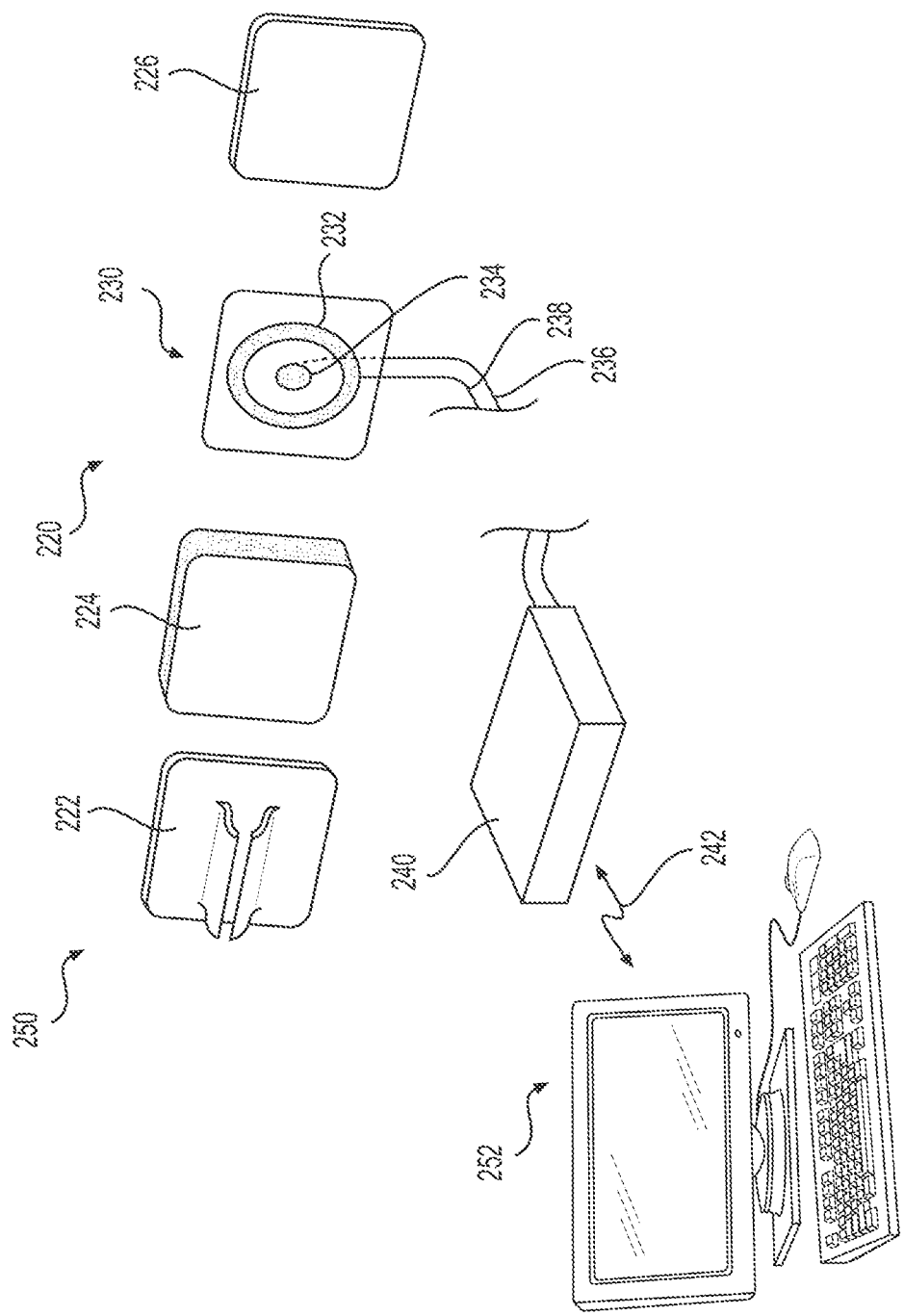

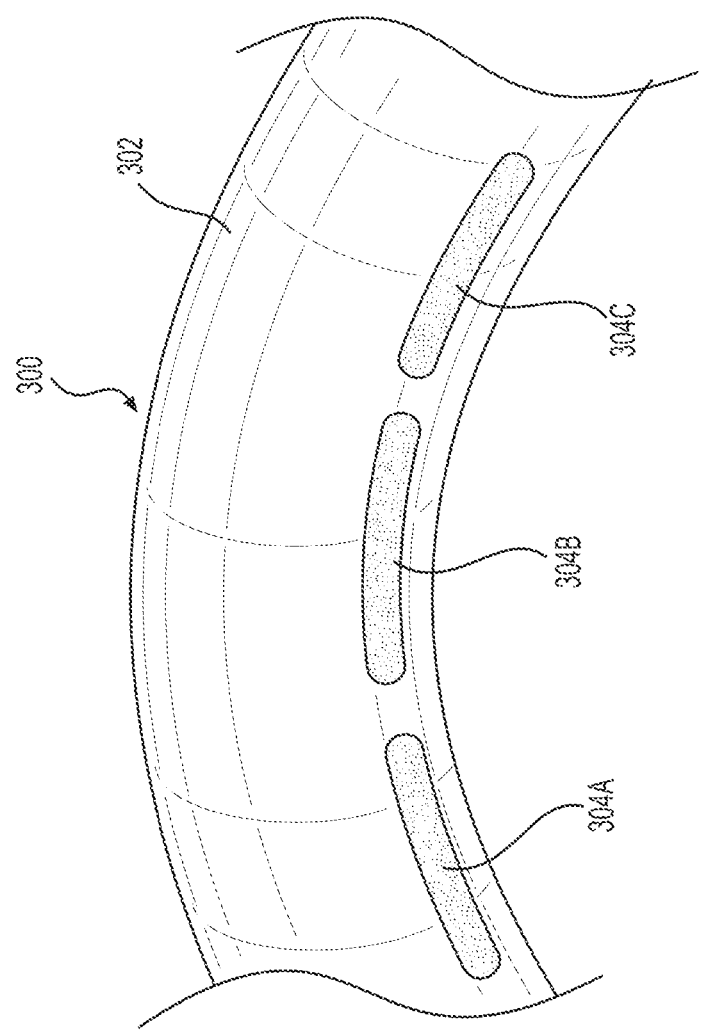

DETECTION OF TISSUE DAMAGE

CROSS-REFERENCE TO RELATED APPLICATION

This application claims the benefit of U.S. Provisional Application No. 62/628,676, which was filed on Feb. 9, 2018, the entirety of which is incorporated herein by reference.

FIELD

The present disclosure provides methods and apparatus for detecting tissue damage through measurement of Sub-Epidermal Moisture (SEM) and evaluation of those measurements.

BACKGROUND

The skin is the largest organ in the human body. It is readily exposed to different kinds of damages and injuries. When the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer.

Patients may be required to use a medical device for an extended period of time to treat a particular condition. Some devices are in contact with portions of the patient's body, for example a tube feeding air to a nasal cannula. Patients who are lying prone in a bed may have devices laying on their body, in some cases taped to the skin to hold the device in place. The long-term pressure applied by these devices may be low but the extended period of application may lead to tissue damage that, left untreated, may progress to an open ulcer.

SUMMARY

In an aspect, the present disclosure provides for, and includes, an apparatus for detecting tissue damage proximate to a point of contact between a medical device and a patient's skin, comprising: a first electrode and a second electrode configured to measure a level of sub-epidermal moisture (SEM) in tissue proximate to the point of contact, an electronics package individually connected to the first and second electrodes and configured to measure a capacitance between the first and second electrodes.

In an aspect, the present disclosure provides for, and includes, a method for detecting tissue damage proximate to a point of contact between a medical device and a patient's skin, comprising the steps of: measuring a plurality of sub-epidermal moisture (SEM) values of tissue proximate to the point of contact at incremental times, comparing the plurality of SEM values, and determining if there is a significant increase in the SEM that indicates that there is tissue damage.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 4B depicts a SEM sensing system, in accordance with the present disclosure.

FIG. 5C is an enlarged view of a portion of the device of FIG. 5B, in accordance with the present disclosure.

DETAILED DESCRIPTION

Figure 1:
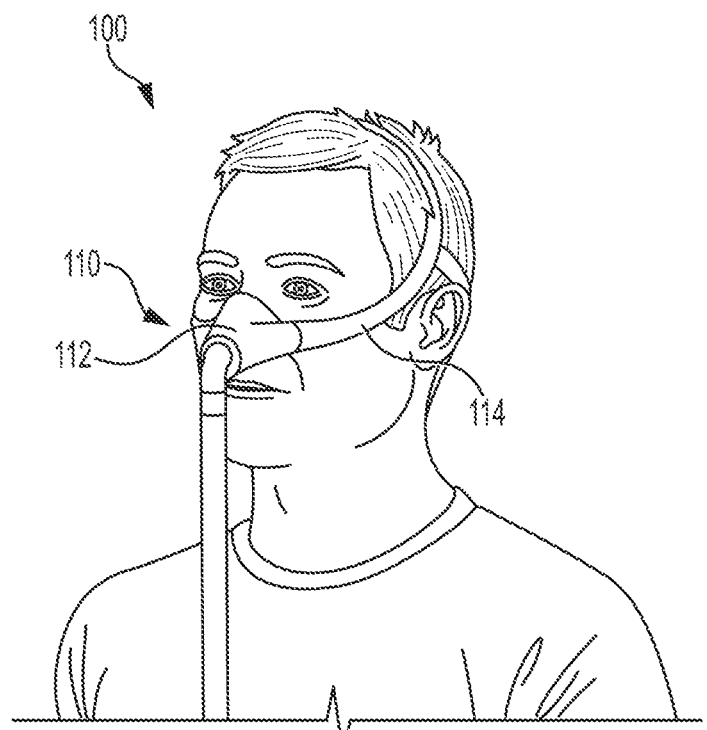
FIG. 1 depicts a patient wearing a Continuous Positive Airway Pressure (CPAP) mask.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 discloses an apparatus that measures the sub-epidermal capacitance using a bipolar sensor, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) similar to the device shown in FIG. 3, where the device emits and receives an RF signal at a frequency of 32 kHz through a single coaxial sensor and generates a bioimpedance signal, then converts this signal to a SEM value.

Both U.S. patent application Ser. Nos. 14/827,375 and 15/134,110 are incorporated herein by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "patient" may be a human or animal subject.

As used herein, "delta" refers to a calculated difference between two SEM values.

FIG. 1 depicts a patient 100 wearing a CPAP mask 110. A CPAP system is used by individuals having difficulty in breathing while sleeping, among others. The mask 110 is worn every night for the entire time that the person is asleep, typically 7-9 hours. This repeated exposure of sensitive facial tissue, where the skin is close to bone, to long-duration low-pressure contact by the nosepiece 112 or straps 114 poses a risk of developing a pressure ulcer.

Figure 2:
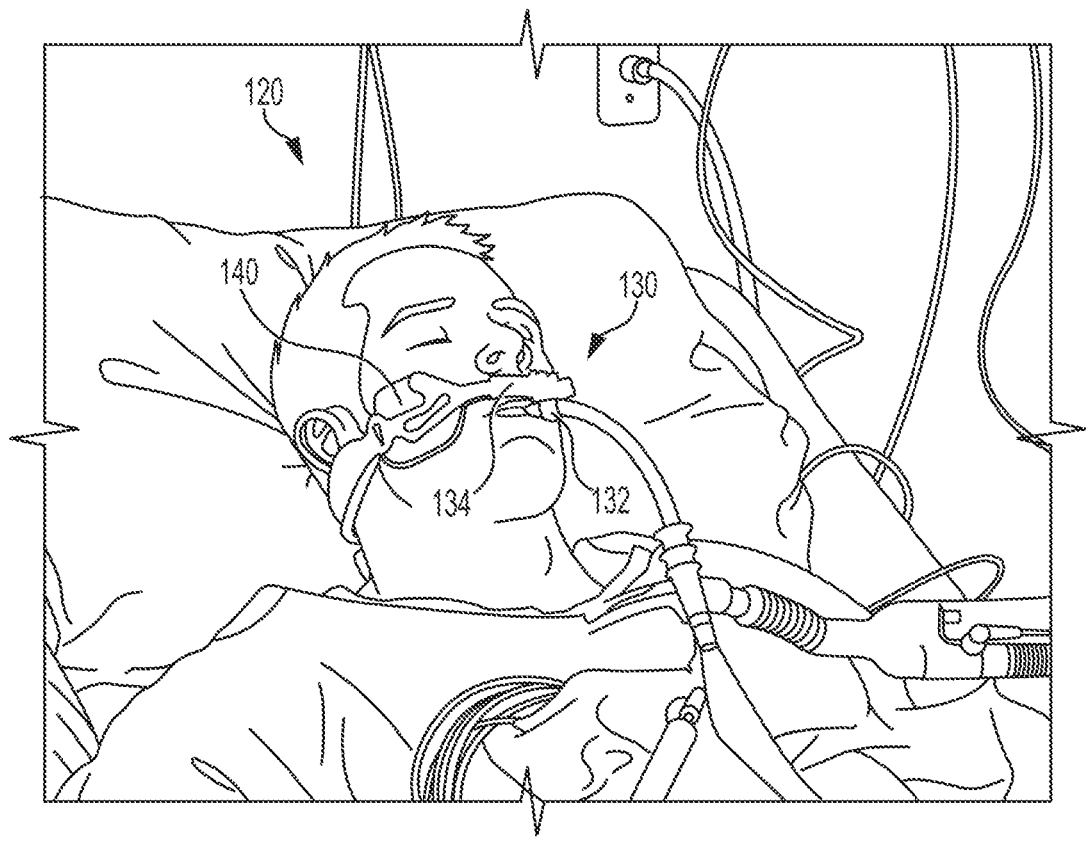
FIG. 2 depicts a patient being treated with a ventilator.

FIG. 2 depicts a patient 120 being treated with a ventilator, which includes mouthpiece 130 having, in this example, an endotracheal tube 132 held in place by a strap 134. Patients that are unable to breathe satisfactorily on their own are "put on" a respirator to ensure that their body is receiving sufficient oxygen to heal. A patient may be on a ventilator for a few hours or a few weeks, depending on the injury. Patients who are on a ventilator for extended periods of time may be put in a medically induced coma because of the discomfort of the ventilator, further reducing their mobility and increasing the risk of a pressure ulcer. In FIG. 2, a pad 140 has been placed on the cheek of the patient 120 and under the strap 134 in order to distribute pressure and protect the skin.

Figure 3A:
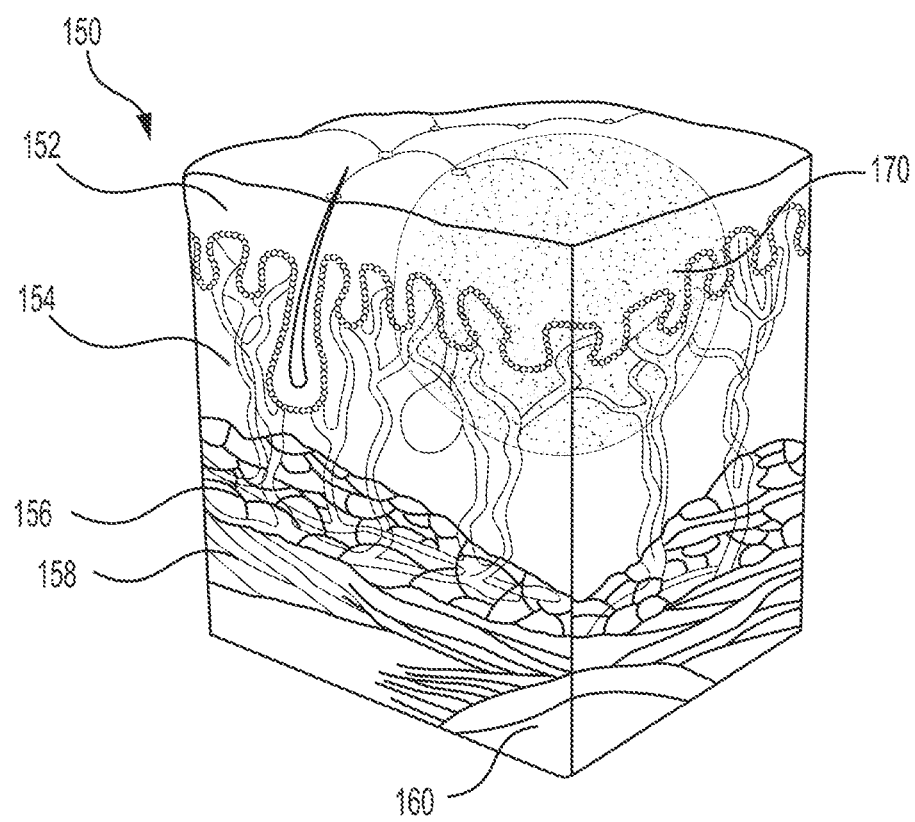
FIG. 3A illustrates the pressure-induced damage associated with a diagnosis of a stage-1 pressure ulcer.

FIG. 3A illustrates the pressure-induced damage associated with a diagnosis of a stage-1 pressure ulcer. This cutaway view of a section of skin tissue 150 shows the top layer stratum corneum, the dermis 154, a layer of fat 156 over a layer of muscle 158, and a bone 160. The darkened region 170 indicates damage to the skin penetrating from the stratum corneum 152 down into the dermis 154. The surface of the skin over region 170 may show a redness and a difference in firmness that can be identified by a trained clinician as a symptom of the damage.

Figure 3B:
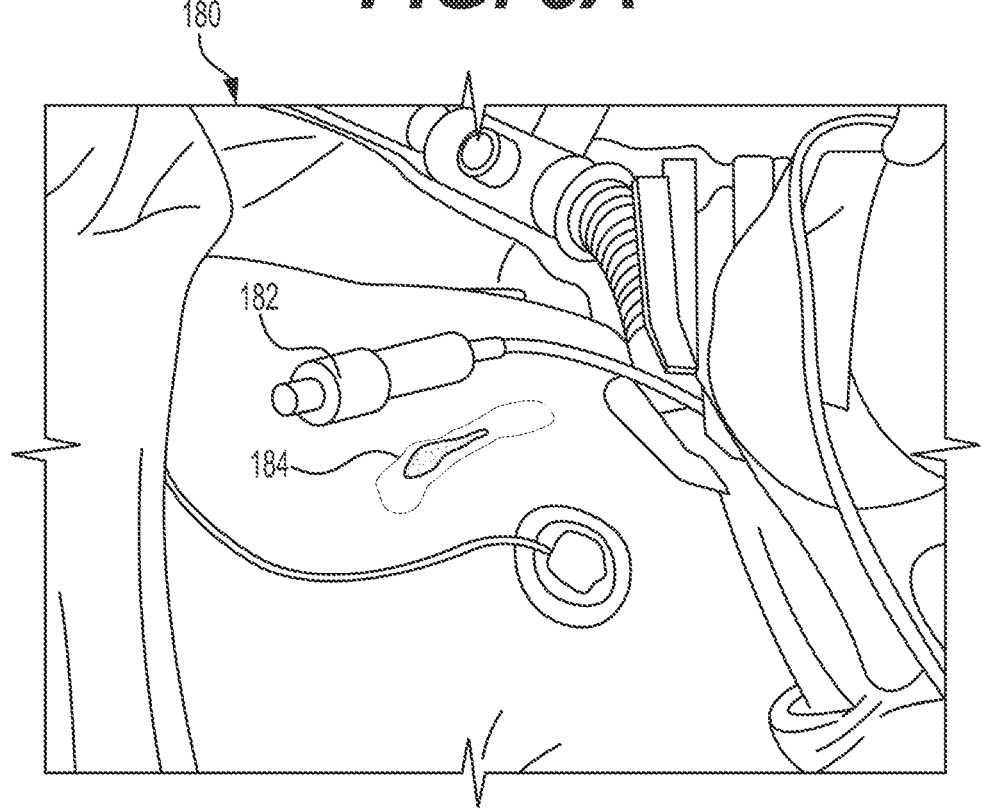
FIG. 3B depicts a patient who has developed a pressure ulcer from a medical device taped to his chest.
Figure 3C:
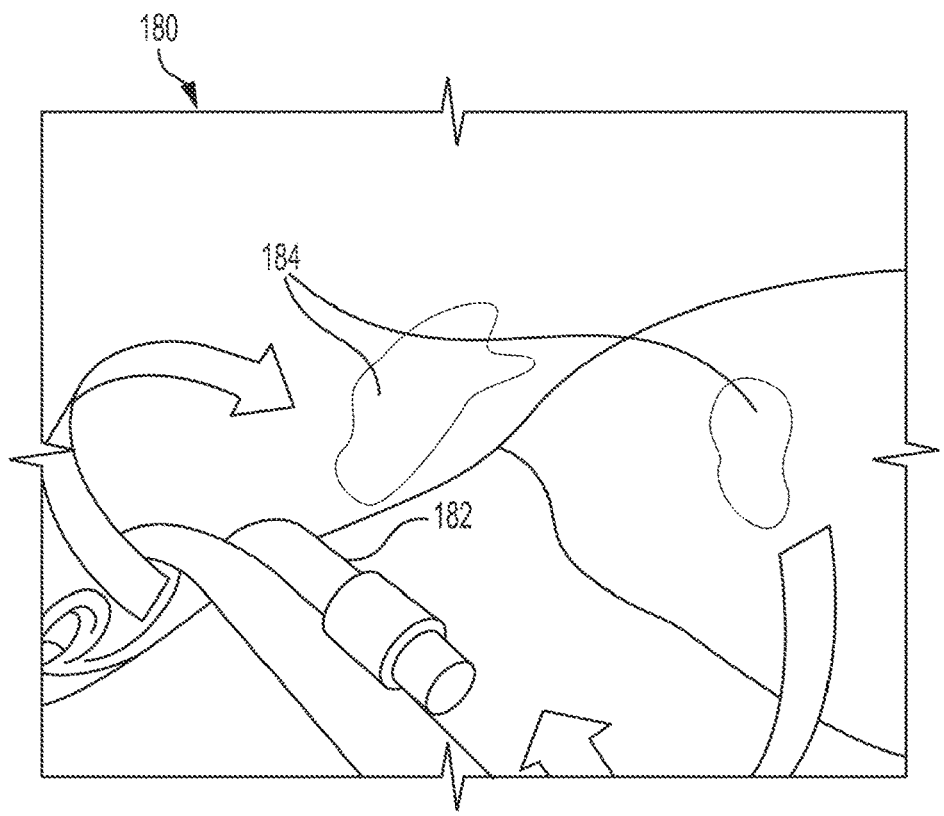
FIGS. 3C and 3D depict patients who developed pressure ulcers from urinary catheters.
Figure 3D:
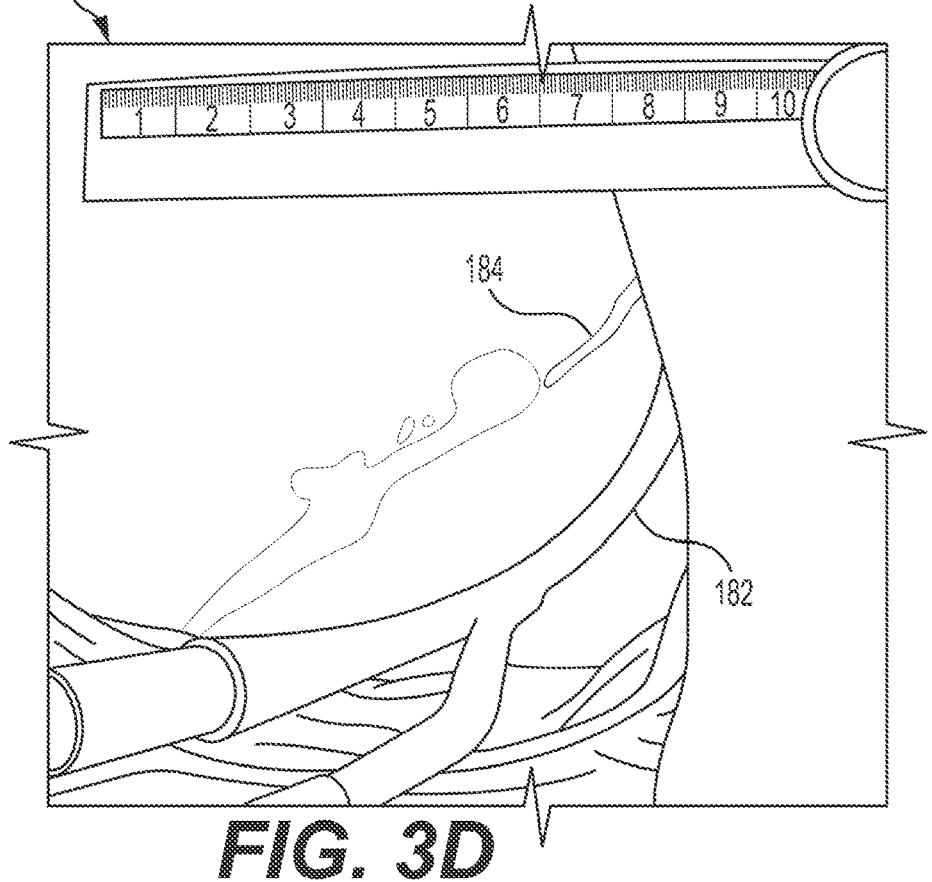

FIG. 3B depicts a patient 180 who has developed a pressure ulcer 184 from a medical device 182 taped to his chest. FIG. 3C depicts a patient 180 who has developed a pressure ulcer 184 in the pubic area from a medical device 182, which is a urinary tube. FIG. 3D depicts a patient 180 who has developed a pressure ulcer 184 in the lower abdomen area from a medical device 182, which is also a urinary tube. Development of this type of injury depends on many factors, including the amount of local pressure on the skin, whether additional pressure was created by other items laying over the device 182, and the duration of the pressure. Development of an ulcer is also affected by the condition of the patient's skin, which depends on the age of the patient and their health.

Figure 4A:
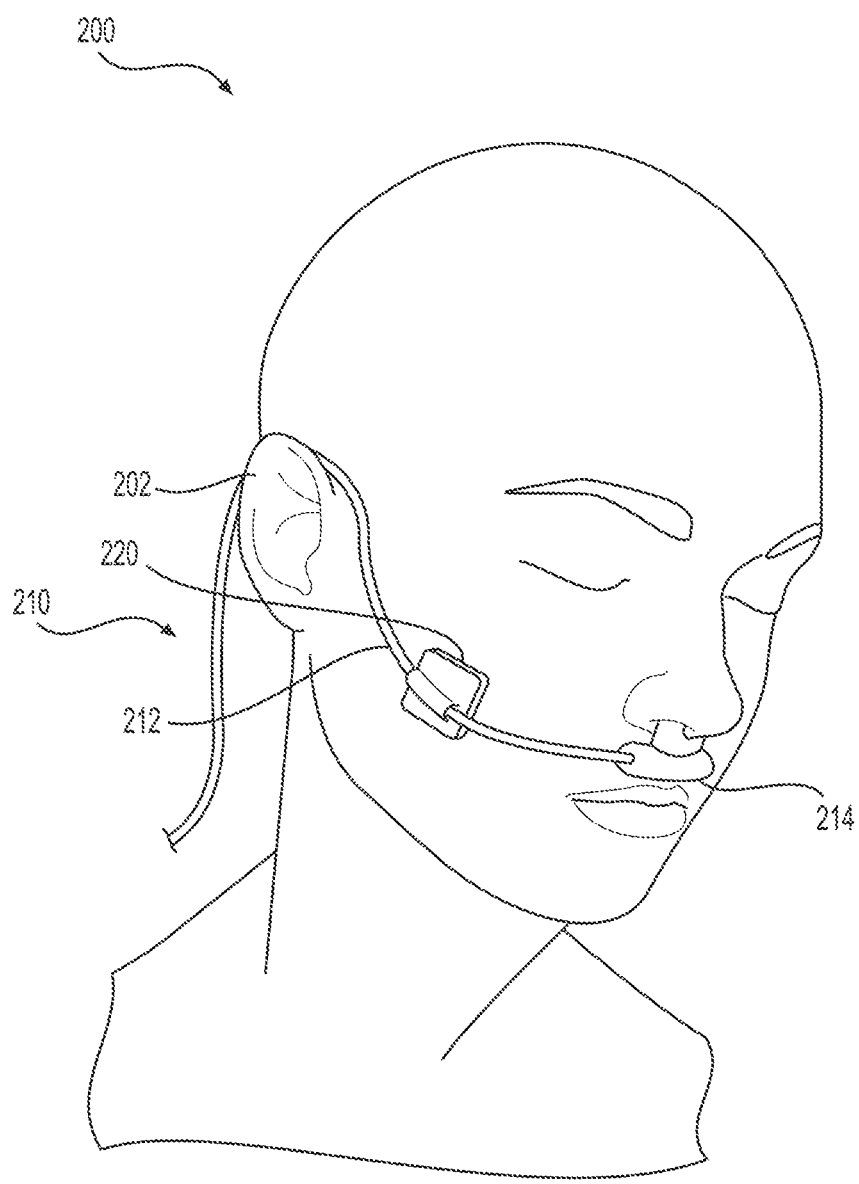
FIG. 4A depicts a patient wearing a medical device with a Sub-Epidermal Moisture (SEM) sensor, in accordance with the present disclosure.

FIG. 4A depicts a patient 200 wearing a medical device 210 with a Sub-Epidermal Moisture (SEM) sensor (not visible in FIG. 4A), in accordance with the present disclosure. There is contact between the device 210 and the patient 200 in multiple locations, such as behind the ear, along the tube 212 over the cheek, at the location of retention device 220, and at the fitting 214 where the tube 212 connects to a nasal cannula (not visible in FIG. 4A). In general, tension on the tube 212 creates pressure in many if not all of these locations.

FIG. 4B depicts an example SEM sensing system 250, in accordance with the present disclosure. The system 250 includes a molded plastic clip 222 configured to attach to the tube 212, a layer of foam 224 to distribute pressure, a SEM sensor 230. In an aspect, there is a layer of adhesive 226 to attach the retention device 220 to the skin of the patient 200. The sensor 230 has electrodes 232, 234 that are connected via wires 236, 238 to electronics package 240, which is configured to make a measurement of the capacitance between the two electrodes 232, 234 and calculate a "delta" value that is, in one aspect, the difference between the highest SEM value and the lowest SEM value in a set of measurements. In an aspect, a set of measurements is taken during a single clinical evaluation. In one aspect, a set of measurements is taken over time, with the first measurement taken at the time of the first use of the medical device.

In an aspect, a calculated delta value is compared to a threshold. When the delta value exceeds the threshold, this indicates a degree of damage. There may be multiple thresholds used to evaluate multiple levels of tissue damage. In one aspect, the maximum SEM value is compared to a threshold. When the maximum value exceeds the threshold, this indicates a degree of damage.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value based on a given unit of SEM. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, the electronics package 240 includes devices to communicate over link 242 to computer 252, which may be a PC, a mobile tablet, a mobile phone, a server using cloud-based data storage and analysis, or other data systems. Link 242 may include a wired or wireless communication element, optical communication elements, a network that may have one or more switches and routers, and other standard data transfer devices and protocols. Link 242 may also be implemented as hardware with nonvolatile storage, for example a "thumb drive," that is loaded with data by the electronics package 240 and in turn is physically relocated and connected to the computer 252 whereupon it delivers the data. In an aspect, Link 242 provides real-time communication of recorded SEM measurements and/or calculated delta values from electronic package 240 to computer 252 to allow for real-time monitoring of ulcer development in a patient.

In one aspect, a molded plastic clip 222 of SEM sensing system 250 of the present disclosure is configured to attach to a medical device selected from the group consisting of a nasogastric tube, a feeding tube, an endotracheal tube, a tracheostomy tube, a tracheostomy collar, a nasal cannula, an IV/PICC line, a central line, a catheter, and a fecal management tube. In an aspect, adhesive 226 has a shape selected from the group consisting of substantially a square, substantially a rectangle, substantially a circle, and a polygon. In one aspect, a face of adhesive 226 has a surface area less than 25 $cm^2$, such as less than 20 $cm^2$, less than 15 $cm^2$, less than 10 $cm^2$, or less than 5 $cm^2$. In an aspect, SEM sensing system 250 has a mass of less than 5 grams, such as less than 4 grams, less than 3 grams, less than 2 grams, less than 1 gram, or less than 0.5 gram.

Figure 5A:
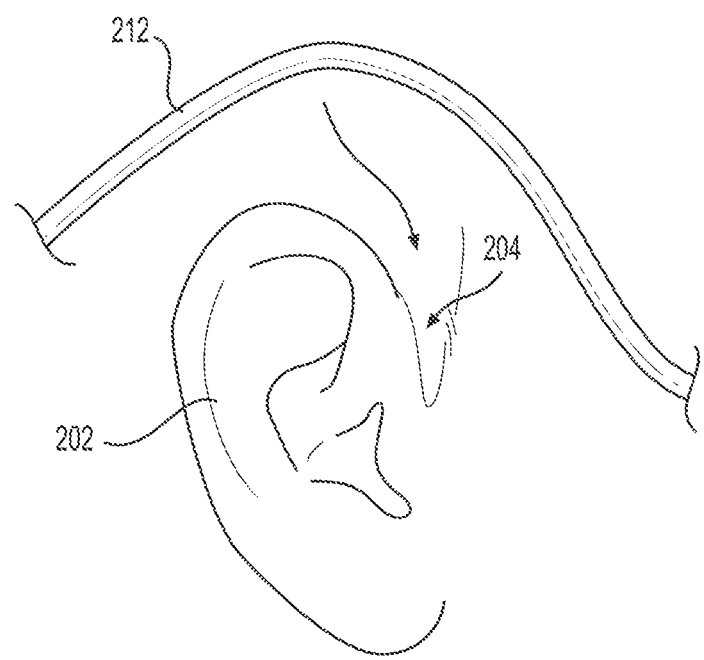
FIG. 5A illustrates how a medical device may contact a patient.

FIG. 5A illustrates how a medical device may contact a patient. The tube 212 from FIG. 4A runs over the crease 204 between a patient's ear 202 and their skull. Pressure can develop at the point of contact between tube 212 and the crease 204 due to tension in tube 212.

Figure 5B:
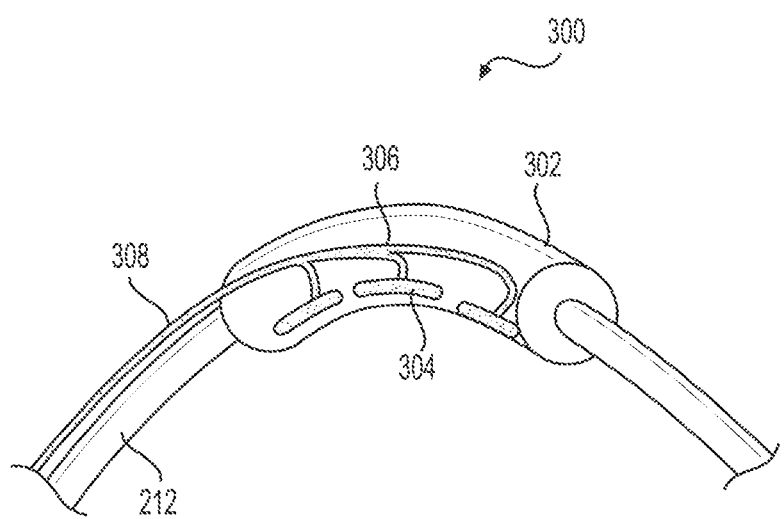
FIG. 5B depicts a SEM sensing device, in accordance with the present disclosure.

FIG. 5B depicts a SEM sensing device 300, in accordance with the present disclosure. In an aspect, the device 300 is added to a basic medical device, for example tube 212. Electrodes 304 on the external surface of the device body 302 are connected by wires 306 of cable 308 to an external electronics package (not shown in FIG. 5B). In an aspect, the device 300 comprises a processor (not visible in FIG. 5B) that does one or more of switching, sensing, and measurement. In an aspect, the processor provides wireless communication to the electronics package. In one aspect, the wireless communication to the electronics package from the electrodes occurs in real-time. In an aspect, the wireless communication to the electronics package is delayed.

FIG. 5C is an enlarged view of a portion of the device 300 of FIG. 5B, in accordance with the present disclosure. In this example, there are three electrodes 304A, 304B, and 304C that are aligned in a row on the surface of body 302, but this array of electrodes may utilize two or more electrodes that are disposed in any two-dimensional pattern. In an aspect, device 300 may comprise three or more electrodes, such as four or more electrodes, five or more electrodes, ten or more electrodes, fifteen or more electrodes, twenty or more electrodes, twenty-five or more electrodes, thirty or more electrodes, forty or more electrodes, or fifty or more electrodes.

In FIG. 5C, electrodes 304A, 304B, 304C are elongated rectangles with rounded ends, but these electrodes may be provided in any shape and size. In an aspect, electrodes 304A, 304B, and 304C may be any shape or configuration, such as point electrodes, plate electrodes, ring electrodes, hexagonal electrodes, or interdigitated finger electrodes. In this example, the long, thin aspect ratio of the electrodes over the curved body 302 provides for complete contact between each electrode 304A, 304B, 304C and the patient's skin. In one aspect, electrodes of device 300 are approximately evenly spaced apart by from about 0.1 cm to about 5 cm, such as from about 0.2 cm to about 5 cm, from about 0.3 cm to about 5 cm, from about 0.4 cm to about 5 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 0.1 cm to about 4.5 cm, from about 0.1 cm to about 4 cm, from about 0.1 cm to about 3.5 cm, from about 0.1 cm to about 3 cm, from about 0.1 cm to about 2.5 cm, from about 0.1 cm to about 2 cm, from about 0.1 cm to about 1.5 cm, from about 0.1 cm to about 1 cm, from about 0.1 cm to about 0.9 cm, from about 0.1 cm to about 0.8 cm, from about 0.1 cm to about 0.7 cm, from about 0.1 cm to about 0.6 cm, from about 0.1 cm to about 0.5 cm, from about 0.1 cm to about 0.4 cm, from about 0.1 cm to about 0.3 cm, from about 0.1 cm to about 0.2 cm, from about 0.5 cm to about 4.5 cm, from about 1 cm to about 4 cm, from about 1.5 cm to about 3.5 cm, or from about 2 cm to about 3 cm. In an aspect, there is an insulating cover layer over each of the electrodes 304A, 304B, 304C.

Still referring to FIG. 5C, the electrodes 304A, 304B, 304C are individually coupled to the electronics package or other controlling processor such that pairs of any two electrodes may be selected to form a two-electrode sensor. With an array of electrodes, a plurality of sensors may be formed to measure capacitance over a region without moving the device 300. For example, electrodes 304A, 304B can be paired to measure the SEM in the tissue between the electrodes 304A, 304B, then electrodes 304B, 304C can be paired to measure the SEM in the tissue between the electrodes 304B, 304C.

In an aspect, device 300 of the present disclosure is configured to attach to a medical device selected from the group consisting of a nasogastric tube, a feeding tube, an endotracheal tube, a tracheostomy tube, a nasal cannula, an IV/PICC line, a central line, a catheter, and a fecal management tube. In one aspect, device 300 has a mass of less than 5 grams, such as less than 4 grams, less than 3 grams, less than 2 grams, less than 1 gram, or less than 0.5 gram.

Figure 6A:
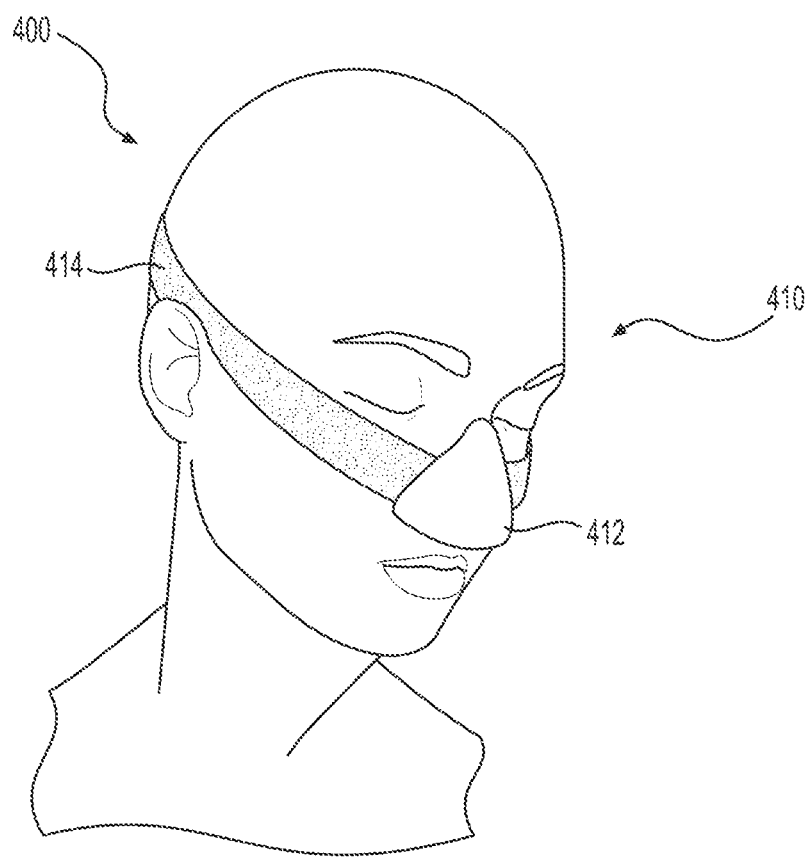
FIG. 6A depicts a patient wearing a medical device that incorporates an elastic retention strap, in accordance with the present disclosure.

FIG. 6A depicts a patient 400 wearing a medical device 410 that incorporates a retention strap 414 to hold nosepiece 412 in place, in accordance with the present disclosure. In order to function, there must be tension in the elastic strap 414 and along the contact edges of nosepiece 412.

Figure 6B:
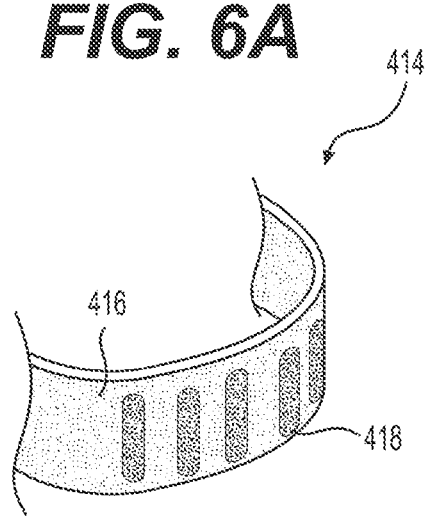
FIG. 6B is an enlarged view of a portion of the retention strap of FIG. 6A, in accordance with the present disclosure.

FIG. 6B is an enlarged view of a portion of the retention strap 414 of FIG. 6A, in accordance with the present disclosure. In this example, electrodes 418 are attached to the elastic 416 such that the electrodes 418 are in contact with the patient's skin while the device 410 is worn. In one aspect, electrodes 418 are elongated-shaped electrodes. In an aspect, similar electrodes (not shown in FIG. 6B) are located on the contact surface of the nosepiece. As described with respect to FIG. 5C, the individual electrodes of an array of electrodes 418 can be connected in various pairs to form sensors. In an aspect, the retention strap 414 includes one or more of a battery, a processor, data storage, and a communication element.

In an aspect, retention strap 414 may comprise two or more electrodes, such as three or more electrodes, four or more electrodes, five or more electrodes, ten or more electrodes, fifteen or more electrodes, twenty or more electrodes, twenty-five or more electrodes, thirty or more electrodes, forty or more electrodes, fifty or more electrodes or a hundred or more electrodes.

In one aspect, electrodes of retention strap 414 are approximately evenly spaced apart by from about 0.1 cm to about 5 cm when the retention strap is in a relaxed state, such as from about 0.2 cm to about 5 cm, from about 0.3 cm to about 5 cm, from about 0.4 cm to about 5 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 0.1 cm to about 4.5 cm, from about 0.1 cm to about 4 cm, from about 0.1 cm to about 3.5 cm, from about 0.1 cm to about 3 cm, from about 0.1 cm to about 2.5 cm, from about 0.1 cm to about 2 cm, from about 0.1 cm to about 1.5 cm, from about 0.1 cm to about 1 cm, from about 0.1 cm to about 0.9 cm, from about 0.1 cm to about 0.8 cm, from about 0.1 cm to about 0.7 cm, from about 0.1 cm to about 0.6 cm, from about 0.1 cm to about 0.5 cm, from about 0.1 cm to about 0.4 cm, from about 0.1 cm to about 0.3 cm, from about 0.1 cm to about 0.2 cm, from about 0.5 cm to about 4.5 cm, from about 1 cm to about 4 cm, from about 1.5 cm to about 3.5 cm, or from about 2 cm to about 3 cm.

In an aspect, retention strap 414 of the present disclosure is configured to function as a tracheostomy strap. In one aspect, retention strap 414 of the present disclosure is configured to function as an abdominal binder. In an aspect, retention strap 414 of the present disclosure is configured to attach to an oxygen delivery mask. In one aspect, retention strap 414 of the present disclosure is configured to attach to an identification band.

In one aspect, a face of retention strap 414 has a surface area less than 6000 $cm^2$, such as less than 5000 $cm^2$, less than 4000 $cm^2$, less than 3000 $cm^2$, less than 2000 $cm^2$, less than 1000 $cm^2$, less than 500 $cm^2$, less than 100 $cm^2$, less than 50 $cm^2$, less than 25 $cm^2$, less than 20 $cm^2$, less than 15 $cm^2$, less than 10 $cm^2$, or less than 5 $cm^2$.

Figure 7A:
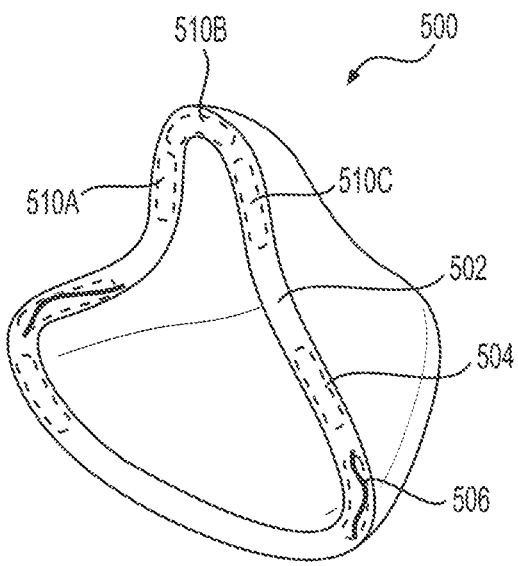
FIGS. 7A and 7B depict example medical devices with controllable pressure management elements, in accordance with the present disclosure.

FIG. 7A depicts an example medical device 500 with controllable pressure management elements, in accordance with the present disclosure. In this example, the medical device 500 is a breathing mask that is representative of all devices where the application element is in long-term contact with the skin of a patient. In an aspect, a medical device having an application element in long-term contact with the skin of a patient is a collar or a cast. In one aspect, a medical device having an application element in long-term contact with the skin of a patient is a cervical collar or a cervical cast. In this example, the pressure management elements are inflatable pockets such as pocket 504, which is shown in an inactive, e.g., deflated, state. Pocket 506, by way of comparison, is shown in an active, e.g., inflated, state. When pockets 504, 506 are configured as shown in FIG. 7A, pressure is higher in the region of pocket 506 and lower in the region of pocket 504. In an aspect, the pressure in the region of pocket 504 is low enough to allow blood flow through the tissue of this region.

In an aspect, the pressure management elements are provided in sets such as pockets 510A, 501B, and 510C. These pockets may be manipulated in a coordinated fashion to shift the levels of contact pressure between the device 500 and the skin of the patient in the regions of the pockets 510A, 510B, 510C. For example, the pocket 510B is inflated while pockets 510A, 510C are deflated, creating a relatively high contact pressure area around pocket 510B and a relatively low, e.g. lower than the nominal pressure that would be present in the absence of a pressure management element, contact pressure in the regions of pockets 510A, 510C. This relatively low contact pressure allows adequate blood flow to the tissue in that region so as to avoid tissue damage. At a different time, one or both of pockets 510A, 510C are inflated while pocket 510B is deflated, thus reducing the contact pressure in the region of pocket 510B.

In an aspect, the pockets are flexible membranes that comprise a portion of the walls of a sealed compartment that is within or on the surface of device 500. In an aspect, at least one of the walls of the pockets is stretchable. In one aspect, when the pockets are situated within the surface of device 500, the wall of device 500 that is in contact with the skin of a patient is also stretchable.

The words "force" and "pressure" are considered to be interchangeable within the context of this disclosure. A higher pressure within a pocket will apply a greater pressure over the area of the pocket, which produces a higher total force (pressure×area=force). A greater amount of fluid in the pocket does not intrinsically apply a higher pressure or force; the raised height of the pocket will cause the patient's skin to come in contact with the inflated pocket first and thereby the inflated pocket will provide a greater portion of the total force applied by the device 500 to the patient's skin and such is equivalent to providing a greater pressure and/or force.

Pockets may be fully inflated, fully deflated, or partially inflated to an intermediate pressure. In an aspect, the pockets may be inflated with a gas or a liquid or other fluid. The word "inflation" is interpreted as an indication of pressure or, equivalently, of the amount of fluid within the pocket, such that the phrase "higher inflation" includes the situation of a greater amount of fluid in the compartment.

In an aspect, the pockets are connected to a source of pressurized fluid through elements such as tubing, valves, pressure regulators (not shown in FIG. 7A) that are coupled to and controlled by a controller (not shown in FIG. 7A). In an aspect, the source of pressurized fluid may be the same source of fluid being provided to the patient through the medical device 500, for example pressurized oxygen-enriched air. In an aspect, the controller of the pressure management element is a part of the electronics package 240 of FIG. 4B.

In an aspect, the pressure management element is a mechanical element whose height can be adjusted. In an aspect, the adjustment is provided with an electrical actuator. In an aspect, the actuator comprises a piezoelectric element that causes a change in the height of the element. In an aspect, the pressure management element is a fixed height element that moves parallel to the skin of the patient such that the contact pressure is increased in the region of contact between the element and the skin and reduced in other regions.

Figure 7B:
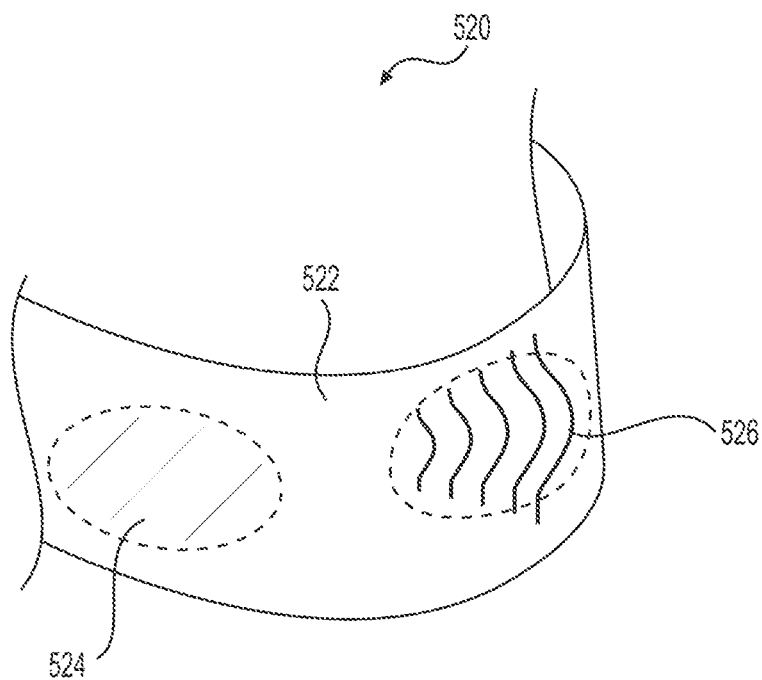

FIG. 7B illustrates another medical device that is a strap 520 similar to the strap 414 shown in FIGS. 6A and 6B. In this example, the strap 520 comprises a band 522 with pockets such as pockets 524, 526 spaced along the band 522. In this example, pocket 524 is inactive and pocket 526 is active, causing the contact pressure under pocket 526 to be higher than the contact pressure under pocket 524. In an aspect, the band 522 is overlaid with an array of electrodes 418 (not visible in FIG. 7B) such that strap 520 can both measure SEM and manage the pressure applied by the strap 520 to the patient's skin.

In an aspect, the change in inflation of the pockets is driven by an SEM reading taken, for example, by the electrodes 418 of FIG. 6B. In one aspect, the change in inflation of the pockets is driven by a delta value that is, in an aspect, the difference between the highest SEM value and the lowest SEM value in a set of measurements. In an aspect, a set of measurements includes measurements taken at a single location. In one aspect, a set of measurements includes measurements taken at multiple locations. In one aspect, a set of measurements is taken at approximately the same time, such as within 10 minutes, within 5 minutes, within 1 minute, within 30 seconds, within 10 seconds, within 5 seconds, or within 1 second. In an aspect, a delta value is calculated by the difference between the most recent SEM value and the cumulative average SEM value over a period of time. In one aspect, a cumulative average SEM value is derived from a set of SEM measurements taken since the first use of the medical device. In an aspect, a cumulative average SEM value is derived from SEM measurements taken within approximately a year, such as within 9 months, within 6 months, within 5 months, within 4 months, within 3 months, within 2 months, within 1 month, within four weeks, within three weeks, within two weeks, within one week, within 6 days, within 5 days, within 4 days, within 3 days, within 2 days, within 1 day, within 16 hours, within 12 hours, within 8 hours, within 4 hours, within 3 hours, within 2 hours, within 1 hour, within 45 minutes, within 30 minutes, within 15 minutes, within 10 minutes, or within 5 minutes.

In an aspect, the change in inflation of the pockets is driven by how a calculated delta value is compared to a threshold. When the delta value exceeds the threshold, inflation pattern of the pockets changes to shift the pressure applied to the patients. There may be multiple thresholds used to determine the inflation pattern of the pockets.

In an aspect, the change in inflation is caused by a timer that regularly shifts the pressure applied to the patient by changing the pattern of active pressure management elements, for example by inflating and deflating different pockets.

In an aspect, a series of predetermined configurations of the pressure management elements are defined and the timer configured to execute a programmed series of changes between these configurations at predefined times. In an aspect, the changes between predetermined configurations are based on SEM readings taken of the patient.

In an aspect, there is a configuration of which pockets are inflated and this default is maintained until a SEM reading indicates a problem, whereupon certain pockets are deflated or reduced in inflation height.

From the foregoing, it will be appreciated that the present invention can be embodied in various ways, which include but are not limited to the following:

Embodiment 1. An apparatus for detecting tissue damage proximate to a point of contact between a medical device and a patient's skin, comprising: a first electrode and a second electrode configured to measure a level of sub-epidermal moisture (SEM) in tissue proximate to the point of contact, an electronics package individually connected to the first and second electrodes and configured to measure a capacitance between the first and second electrodes.

Embodiment 2. The apparatus of embodiment 1, where the first and second electrodes are configured to be attached to the medical device.

Embodiment 3. The apparatus of embodiment 1 or 2, where the first and second electrodes are shaped such that the entire surface of each electrode can contact the patient's skin while the medical device is in use.

Embodiment 4. The apparatus of any one of embodiments 1 to 3, further comprising a body coupled to the first and second electrodes, the body configured to be interposed between the medical device and the patient's skin when the medical device is in use.

Embodiment 5. The apparatus of embodiment 4, where the body is further configured to be attached to the medical device.

Embodiment 6. The apparatus of any one of embodiments 1 to 5, further comprising a communication element configured to provide real-time transfer of SEM measurements to a computing unit.

Embodiment 7. The apparatus of any one of embodiments 1 to 6, where the apparatus is a clip configured to attach to a tube of the medical device.

Embodiment 8. The apparatus of embodiment 7, where the tube is selected from the group consisting of a nasogastric tube, a feeding tube, an endotracheal tube, a tracheostomy tube, a tracheostomy collar, a nasal cannula, an IV/PICC line, a catheter, and a fecal management tube.

Embodiment 9. The apparatus of any one of embodiments 1 to 6, where the apparatus is a strap configured to attach to the medical device.

Embodiment 10. The apparatus of embodiment 9, where the medical device is a mask.

Embodiment 11. The apparatus of any one of embodiments 1 to 6, where the medical device is a collar or a cast.

Embodiment 12. The apparatus of any one of embodiments 1 to 11, where the apparatus further comprises one or more pressure management elements.

Embodiment 13. The apparatus of embodiment 12, where each of the one or more pressure management elements is an inflatable pocket.

Embodiment 14. A method for detecting tissue damage proximate to a point of contact between a medical device and a patient's skin, comprising the steps of: measuring a plurality of sub-epidermal moisture (SEM) values of tissue proximate to the point of contact at incremental times, comparing the plurality of SEM values, and determining if there is a significant increase in the SEM that indicates that there is tissue damage.

Embodiment 15. The method of embodiment 14, where there is a significant increase when the largest SEM value of the plurality of SEM values is greater than the smallest SEM value of the plurality of SEM values by an amount that exceeds a threshold.

Embodiment 16. The method of embodiment 14, where there is a significant increase when the largest SEM value of the plurality of SEM values is greater than a threshold.

Embodiment 17. The method of any one of embodiments 14 to 16, where a first measurement of the SEM value is made at the time of the first use of the medical device.

Embodiment 18. The method of any one of embodiments 14 to 17, where the medical device comprises a tube selected from the group consisting of a nasogastric tube, a feeding tube, an endotracheal tube, a tracheostomy tube, a tracheostomy collar, a nasal cannula, an IV/PICC line, a catheter, and a fecal management tube.

Embodiment 19. The method of any one of embodiments 14 to 17, where the medical device is a mask.

Embodiment 20. The method of any one of embodiments 14 to 17, where the medical device is a collar or a cast.

We claim:

1. An apparatus for detecting tissue damage proximate to a point of contact between a medical device and a patient's skin, comprising:
    a first electrode and a second electrode configured to measure a level of sub-epidermal moisture (SEM) in tissue proximate to the point of contact, and
    an electronics package individually connected to the first and second electrodes and configured to measure a capacitance between the first and second electrodes;
wherein the apparatus is selected from a group consisting of a clip configured to attach to a tube of the medical device, and a strap configured to attach to the medical device.

2. The apparatus of claim 1, wherein the first and second electrodes are configured to be attached to the medical device.

3. The apparatus of claim 1, wherein the first and second electrodes are shaped such that the entire surface of each electrode can contact the patient's skin while the medical device is in use.

4. The apparatus of claim 1, further comprising a body coupled to the first and second electrodes, the body configured to be interposed between the medical device and the patient's skin when the medical device is in use.

5. The apparatus of claim 4, wherein the body is further configured to be attached to the medical device.

6. The apparatus of claim 1, further comprising a communication element configured to provide real-time transfer of SEM measurements to a computing unit.

7. The apparatus of claim 1, wherein the apparatus is a clip configured to attach to a tube of the medical device.

8. The apparatus of claim 1, wherein the tube is selected from the group consisting of a nasogastric tube, a feeding tube, an endotracheal tube, a tracheostomy tube, a tracheostomy collar, a nasal cannula, an IV/PICC line, a catheter, and a fecal management tube.

9. The apparatus of claim 1, wherein the apparatus is a strap configured to attach to the medical device.

10. The apparatus of claim 1, wherein the medical device is a mask.

11. An apparatus for detecting tissue damage proximate to a point of contact between a medical device and a patient's skin, comprising:
    a first electrode and a second electrode configured to measure a level of sub-epidermal moisture (SEM) in tissue proximate to the point of contact, and
    an electronics package individually connected to the first and second electrodes and configured to measure a capacitance between the first and second electrodes;
wherein the medical device is selected from the group consisting of a mask, a collar, and a cast.

12. The apparatus of claim 11, wherein the first and second electrodes are configured to be attached to the medical device.

13. The apparatus of claim 11, wherein the first and second electrodes are shaped such that the entire surface of each electrode can contact the patient's skin while the medical device is in use.

14. The apparatus of claim 11, further comprising a body coupled to the first and second electrodes, the body configured to be interposed between the medical device and the patient's skin when the medical device is in use.

15. The apparatus of claim 14, wherein the body is further configured to be attached to the medical device.

16. The apparatus of claim 11, further comprising a communication element configured to provide real-time transfer of SEM measurements to a computing unit.

17. An apparatus for detecting tissue damage proximate to a point of contact between a medical device and a patient's skin, comprising:
    a first electrode and a second electrode configured to measure a level of sub-epidermal moisture (SEM) in tissue proximate to the point of contact,
    an electronics package individually connected to the first and second electrodes and configured to measure a capacitance between the first and second electrodes, and one or more pressure management elements.

18. The apparatus of claim 17, wherein each of the one or more pressure management elements is an inflatable pocket.

19. The apparatus of claim 17, wherein the first and second electrodes are configured to be attached to the medical device.

20. The apparatus of claim 17, wherein the first and second electrodes are shaped such that the entire surface of each electrode can contact the patient's skin while the medical device is in use.

21. The apparatus of claim 17, further comprising a body coupled to the first and second electrodes, the body configured to be interposed between the medical device and the patient's skin when the medical device is in use.

22. The apparatus of claim 21, wherein the body is further configured to be attached to the medical device.

23. The apparatus of claim 17, further comprising a communication element configured to provide real-time transfer of SEM measurements to a computing unit.

24. A method for detecting tissue damage proximate to a point of contact between a medical device and a patient's skin, comprising the steps of:
    measuring a plurality of sub-epidermal moisture (SEM) values of tissue proximate to the point of contact at incremental times,
    comparing the plurality of SEM values, and
    determining if there is a significant increase in the SEM that indicates that there is tissue damage;
wherein the medical device comprises a tube selected from the group consisting of a nasogastric tube, a feeding tube, an endotracheal tube, a tracheostomy tube, a tracheostomy collar, a nasal cannula, an IV/PICC line, a catheter, and a fecal management tube.

25. The method of claim 24, wherein there is a significant increase when the largest SEM value of the plurality of SEM values is greater than the smallest SEM value of the plurality of SEM values by an amount that exceeds a threshold.

26. The method of claim 24, wherein there is a significant increase when the largest SEM value of the plurality of SEM values is greater than a threshold.

27. The method of claim 24, wherein a first measurement of the SEM value is made at the time of the first use of the medical device.

28. A method for detecting tissue damage proximate to a point of contact between a medical device and a patient's skin, comprising the steps of:
   measuring a plurality of sub-epidermal moisture (SEM) values of tissue proximate to the point of contact at incremental times,
   comparing the plurality of SEM values, and determining if there is a significant increase in the SEM that indicates that there is tissue damage;
   wherein the medical device is selected from the group consisting of a mask, a collar, and a cast.

29. The method of claim 28, wherein there is a significant increase when the largest SEM value of the plurality of SEM values is greater than the smallest SEM value of the plurality of SEM values by an amount that exceeds a threshold.

30. The method of claim 28, wherein there is a significant increase when the largest SEM value of the plurality of SEM values is greater than a threshold.

31. The method of claim 28, wherein a first measurement of the SEM value is made at the time of the first use of the medical device.

* * * * *